United States Patent
Yoshida et al.

(10) Patent No.: US 11,321,829 B2
(45) Date of Patent: May 3, 2022

(54) MEDICAL IMAGE PROCESSING APPARATUS, METHOD FOR PROCESSING MEDICAL IMAGE, AND NON-TRANSITORY COMPUTER MEDIUM STORING COMPUTER PROGRAM

(71) Applicant: CANON MEDICAL SYSTEMS CORPORATION, Otawara (JP)

(72) Inventors: Masaki Yoshida, Yaita (JP); Makoto Yonezawa, Utsunomiya (JP); Kazuyo Saito, Nasushiobara (JP); Hirotaka Ujiie, Nasukarasuyama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 268 days.

(21) Appl. No.: 16/589,339

(22) Filed: Oct. 1, 2019

(65) Prior Publication Data
US 2020/0111208 A1    Apr. 9, 2020

(30) Foreign Application Priority Data

Oct. 5, 2018 (JP) .............................. JP2018-189848
Sep. 24, 2019 (JP) .............................. JP2019-173040

(51) Int. Cl.
| | |
|---|---|
| *G06K 9/00* | (2006.01) |
| *A61B 6/00* | (2006.01) |
| *G06T 7/00* | (2017.01) |
| *A61B 5/055* | (2006.01) |
| *G16H 30/20* | (2018.01) |
| *A61B 5/00* | (2006.01) |
| *G16H 30/40* | (2018.01) |
| *A61B 8/08* | (2006.01) |

(52) U.S. Cl.
CPC ............ *G06T 7/0012* (2013.01); *A61B 5/055* (2013.01); *A61B 5/7207* (2013.01); *G16H 30/20* (2018.01); *G16H 30/40* (2018.01); *A61B 6/466* (2013.01); *A61B 8/483* (2013.01); *A61B 8/5215* (2013.01)

(58) Field of Classification Search
USPC ....... 382/100, 103, 106, 128–132, 154, 168, 382/173, 181, 189, 199, 220, 224, 254, 382/274, 276, 286, 291, 305, 318, 294; 730/2; 378/4, 5, 15, 21
See application file for complete search history.

(56) References Cited

U.S. PATENT DOCUMENTS

| | | | | |
|---|---|---|---|---|
| 6,038,278 A | * | 3/2000 | Hsieh ..................... | A61B 6/032 378/15 |
| 2007/0133736 A1 | * | 6/2007 | Chen ....................... | A61B 6/00 378/5 |

(Continued)

FOREIGN PATENT DOCUMENTS

JP        2017-86562 A     5/2017

*Primary Examiner* — Seyed H Azarian
(74) *Attorney, Agent, or Firm* — Oblon, McClelland, Maier & Neustadt, L.L.P.

(57) ABSTRACT

A medical image processing apparatus according to present embodiments includes processing circuitry. The processing circuitry is configured to acquire medical images. The processing circuitry is configured to control the medical images based on an evaluation value corresponding to each of the medical images, thereby control a forwarding/reversing number or a forwarding/reversing speed of displayed images of the medical images for an operation amount.

20 Claims, 13 Drawing Sheets

(56) References Cited

U.S. PATENT DOCUMENTS

| 2007/0265813 | A1* | 11/2007 | Unal | G06T 7/12 |
|---|---|---|---|---|
| | | | | 703/2 |
| 2017/0065239 | A1* | 3/2017 | Higuma | A61B 6/032 |
| 2018/0174335 | A1* | 6/2018 | Yamakawa | G06T 11/006 |

* cited by examiner

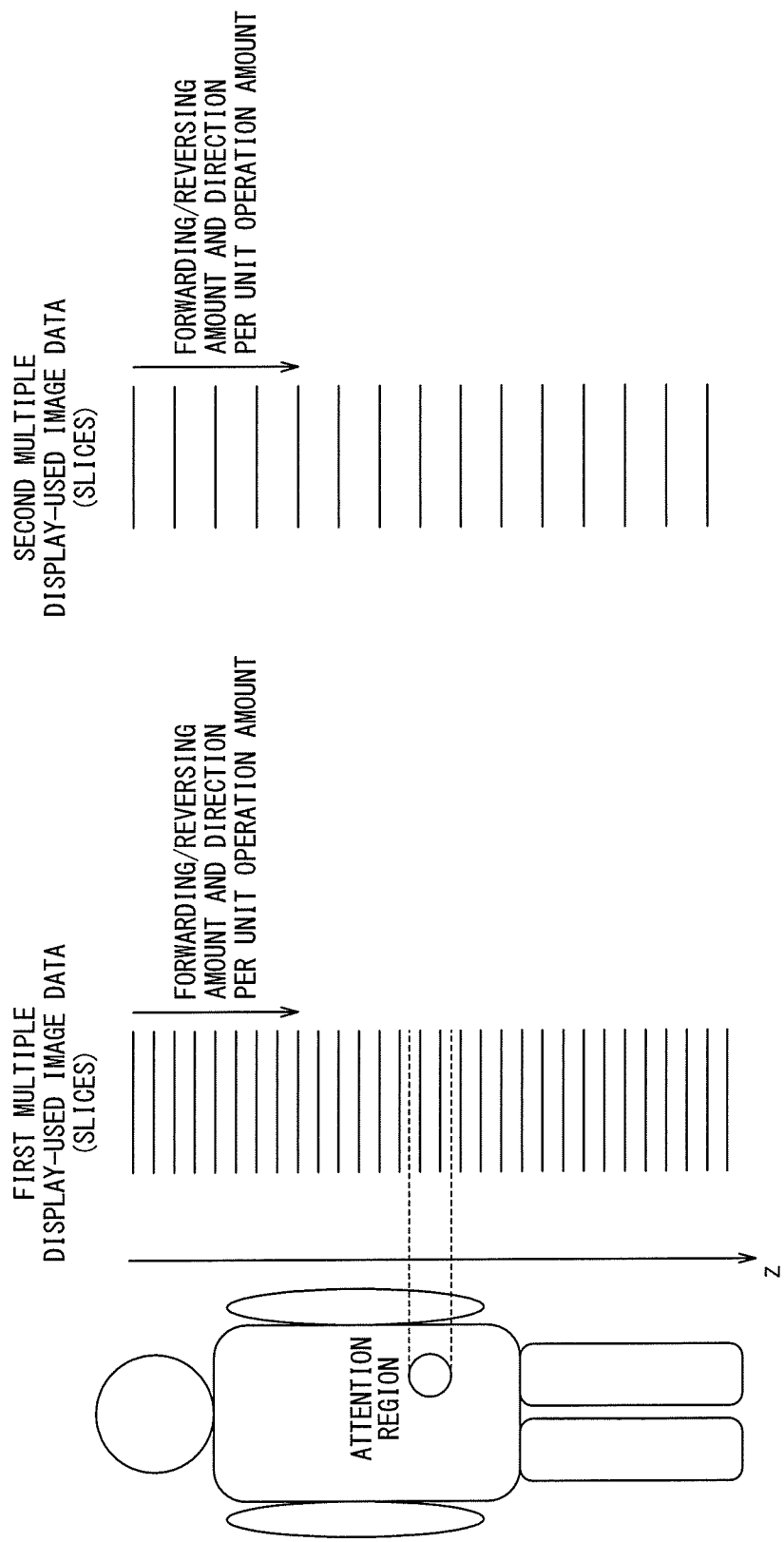

US 11,321,829 B2

MEDICAL IMAGE PROCESSING APPARATUS, METHOD FOR PROCESSING MEDICAL IMAGE, AND NON-TRANSITORY COMPUTER MEDIUM STORING COMPUTER PROGRAM

CROSS-REFERENCE TO RELATED APPLICATION

This application is based upon and claims the benefit of priority from Japanese Patent Application No. 2018-189848, filed on Oct. 5, 2018, Japanese Patent Application No. 2019-173040, filed on Sep. 24, 2019, the entire contents of each of which are incorporated herein by reference.

FIELD

An embodiment as an aspect of the present invention relates to a medical image processing apparatus, a method for processing a medical image and a non-transitory computer readable medium storing a computer program.

BACKGROUND

Conventionally, in the medical field, a medical image diagnostic apparatus images an inside of a subject by using radiation such as X-rays, ultrasonic, nuclear magnetic resonance, etc. The medical image diagnostic apparatus provides a medical image showing the inside of the subject acquired by imaging to a medical image processing apparatus or the like.

An operator such as a doctor may browse medical images using the medical image processing apparatus. For example, the medical images relate to different imaging times or different slices.

Figure 7A:
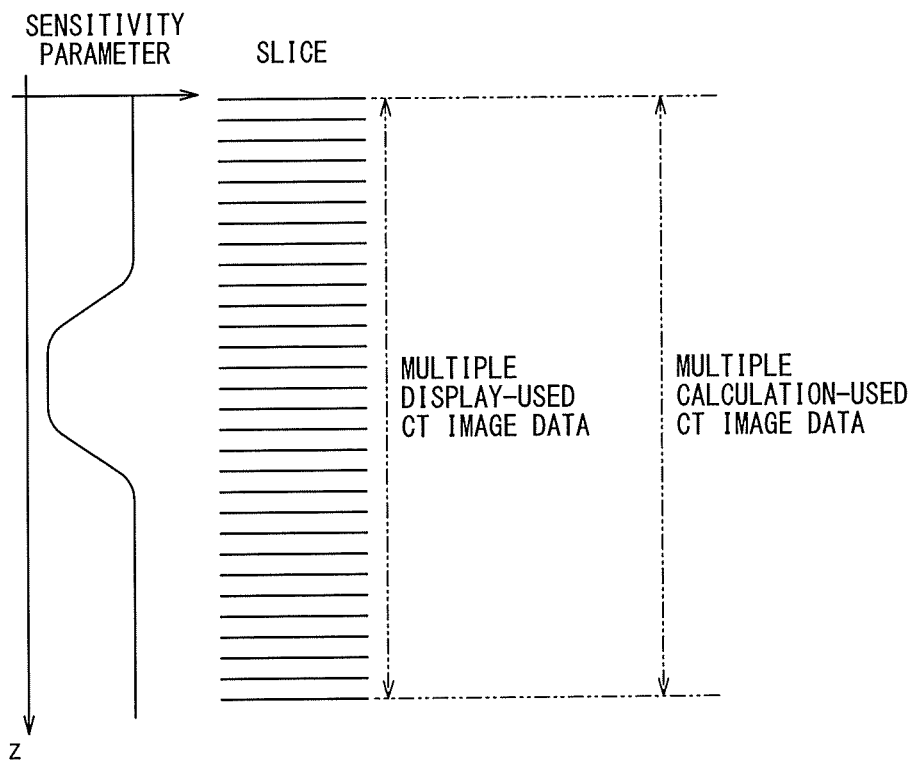
Figure 7B:
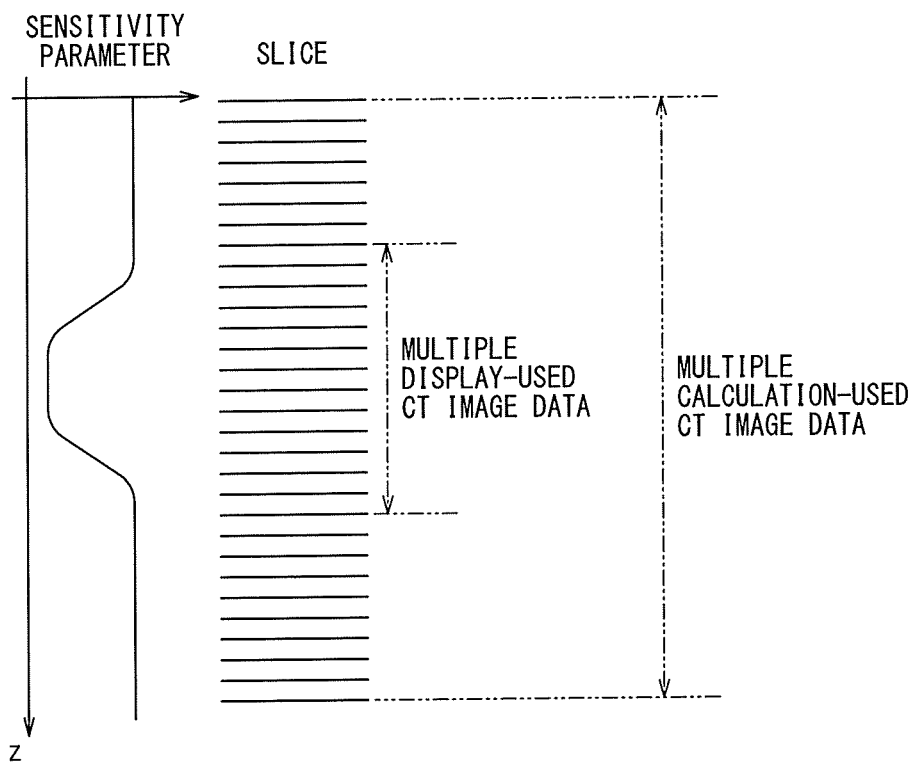

Each of FIGS. 7A and 7B is a diagram showing a relationship between multiple calculation-used CT image data and multiple display-used CT image data in the X-ray CT apparatus including the medical image processing apparatus according to the first embodiment.

Figure 8:
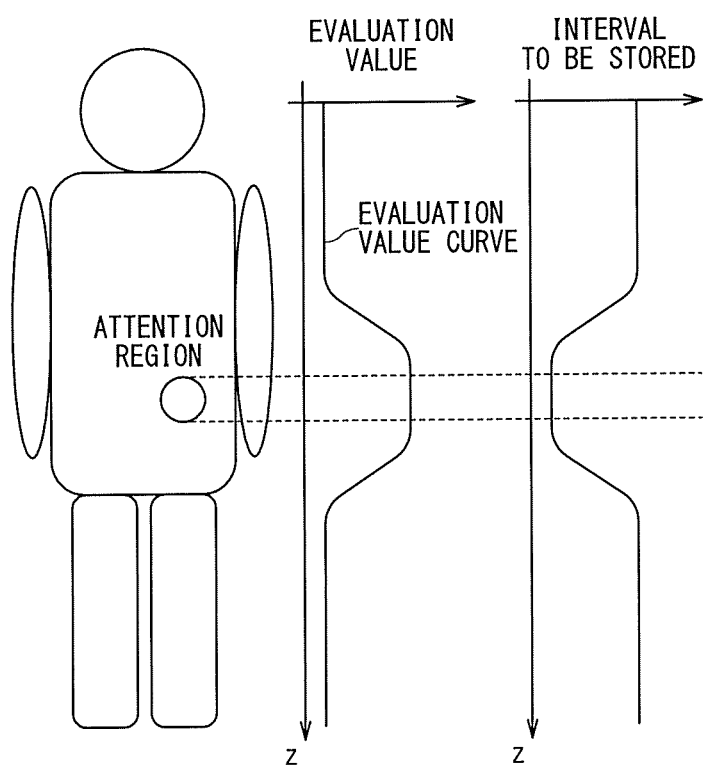

FIG. 8 is a diagram showing a relationship between the evaluation value and the interval to be stored in the X-ray CT apparatus including the medical image processing apparatus according to the first embodiment.

Figure 9:
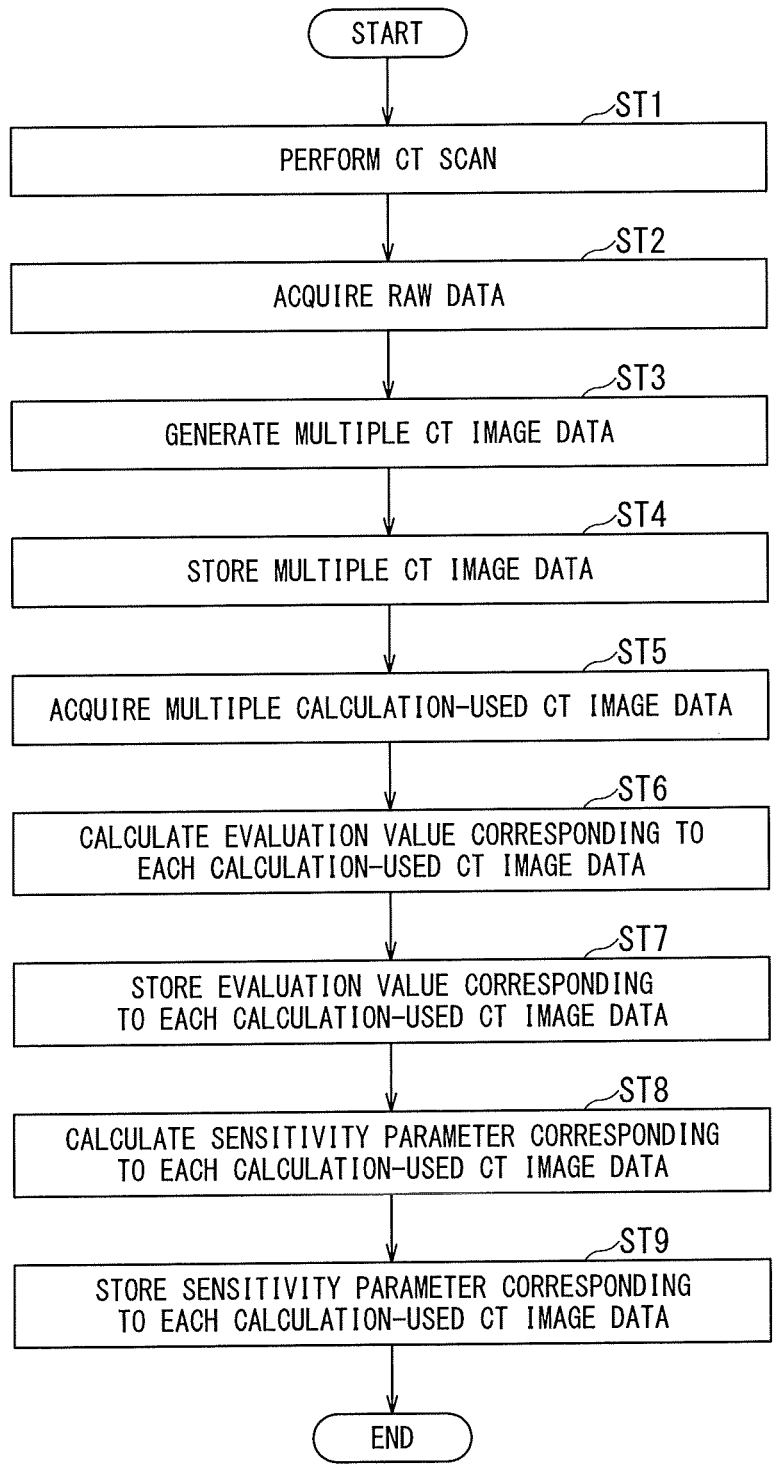

FIG. 9 is a diagram showing an operation of the X-ray CT apparatus including the medical image processing apparatus according to the first embodiment as a flowchart.

Figure 10:
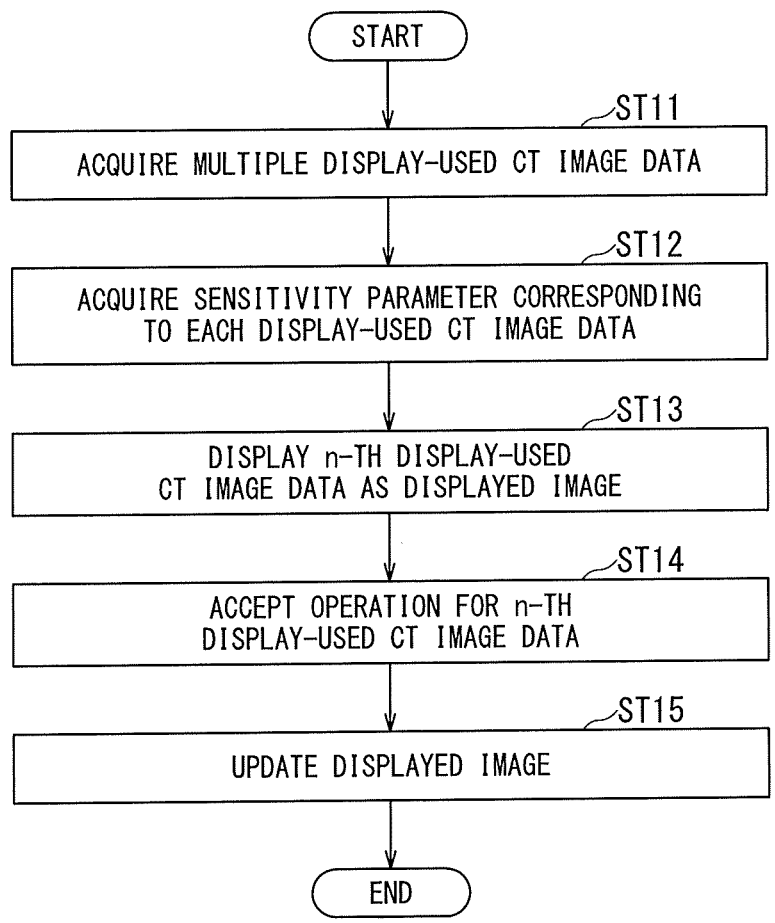

FIG. 10 is a diagram showing an operation of the X-ray CT apparatus including the medical image processing apparatus according to the first embodiment as a flowchart.

Figure 11:
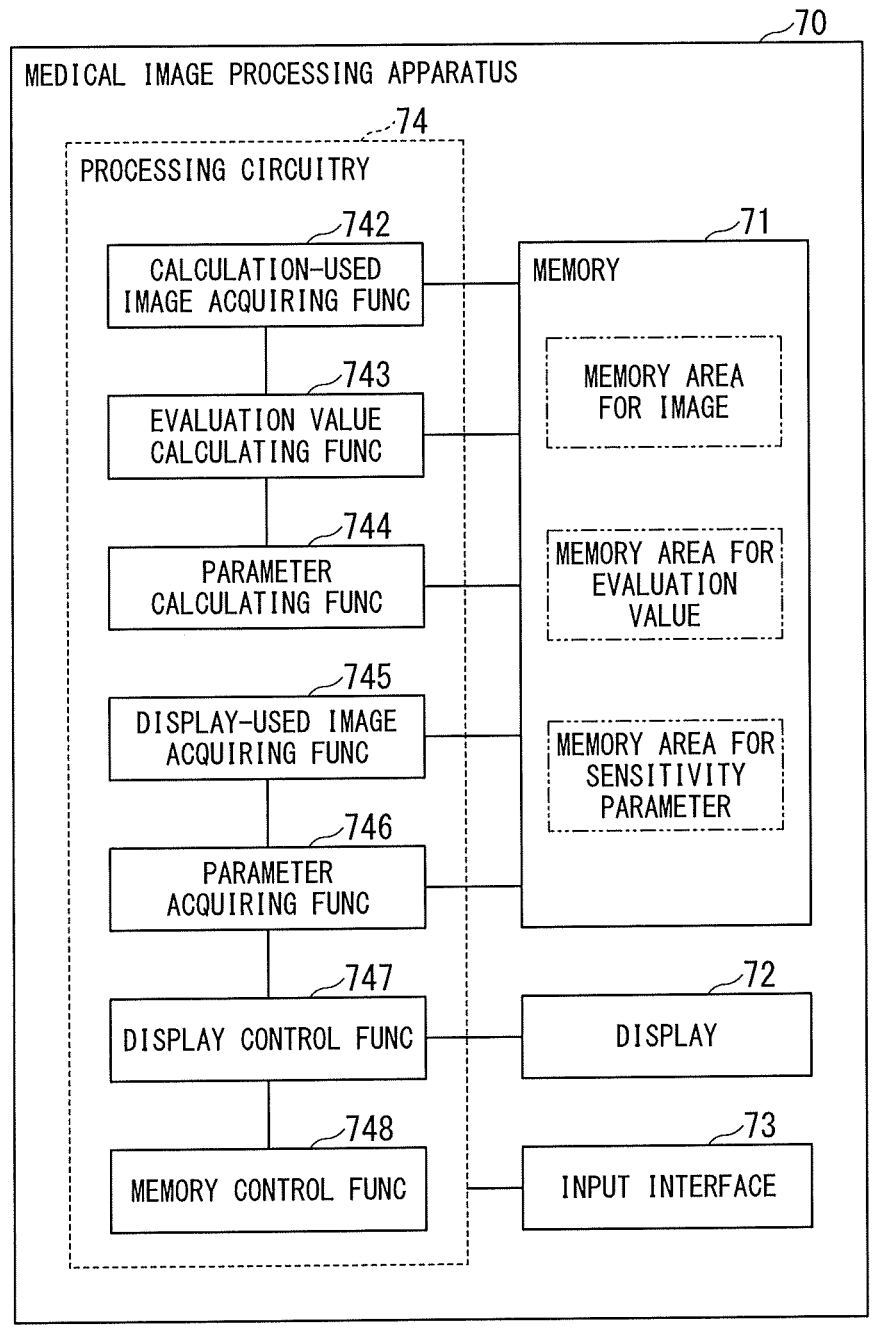

FIG. 11 is a block diagram showing a configuration and functions of a medical image processing apparatus according to a second embodiment.

FIG. 12 is a diagram for explaining adjustment of the sensitivity parameter in the medical image processing apparatus according to the second embodiment.

Figure 13B:
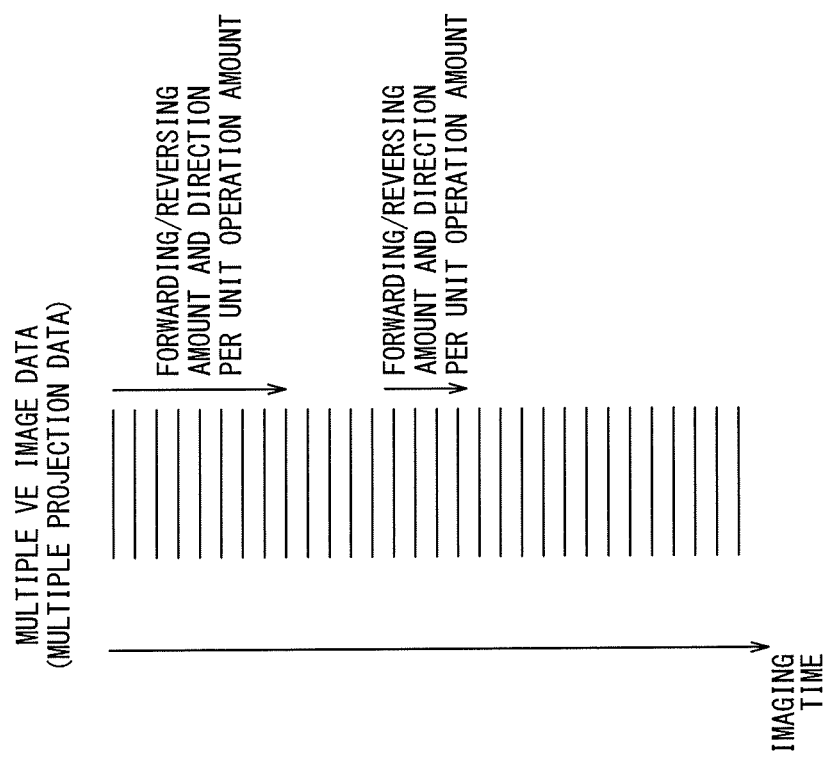
Figure 13A:
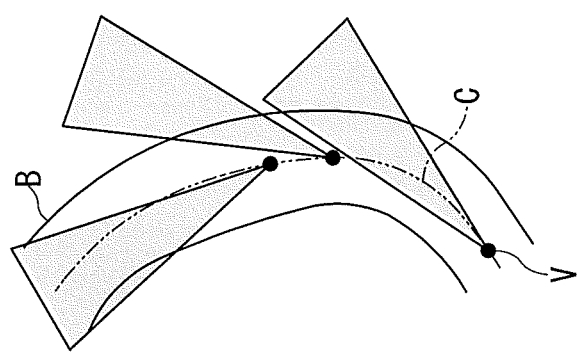

Each of FIGS. 13A and 13B is a diagram for explaining sensitivity parameters for multiple three-dimensional image data having different positions and imaging times in the medical image processing apparatus according to the second embodiment.

DETAILED DESCRIPTION

A medical image processing apparatus, a method for processing a medical image and a non-transitory computer readable medium storing a computer program according to present embodiments will be described by referring to the accompanying drawings.

A medical image processing apparatus according to present embodiments includes processing circuitry. The processing circuitry is configured to acquire medical images. The processing circuitry is configured to control the medical images based on an evaluation value corresponding to each of the medical images, thereby control a forwarding/reversing number or a forwarding/reversing speed of displayed images of the medical images for an operation amount.

1. Medical Image Processing Apparatus According to First Embodiment

A medical image processing apparatus according to a first embodiment is provided in a medical image diagnostic apparatus. Examples of the medical image diagnostic apparatus are an X-ray computed tomography (CT) apparatus, a nuclear medicine diagnostic apparatus such as a positron emission tomography (PET) apparatus, and a magnetic resonance imaging (MRI) apparatus. That is, the medical image processing apparatus according to the first embodiment functions as a console which acquires medical images. Hereinafter, a case where the medical image processing apparatus according to the first embodiment is provided in the X-ray CT apparatus as the medical image diagnostic apparatus will be described as an example.

There are various types for data acquisition by the X-ray CT apparatus, such as a rotate/rotate (R-R) method and a stationary/rotate (S-R) method. In the rotate/rotate type, the X-ray source and the X-ray detector integrally rotate around a subject. In the stationary/rotate type, multiple detection elements are annually arrayed and only the X-ray tube is rotated around the subject. The present invention can be applied to either type. Hereinafter, a description will be given of a case where the third generation rotate/rotate type currently occupying the mainstream is adopted for the radiographic diagnosis according to the embodiment.

Figure 1:
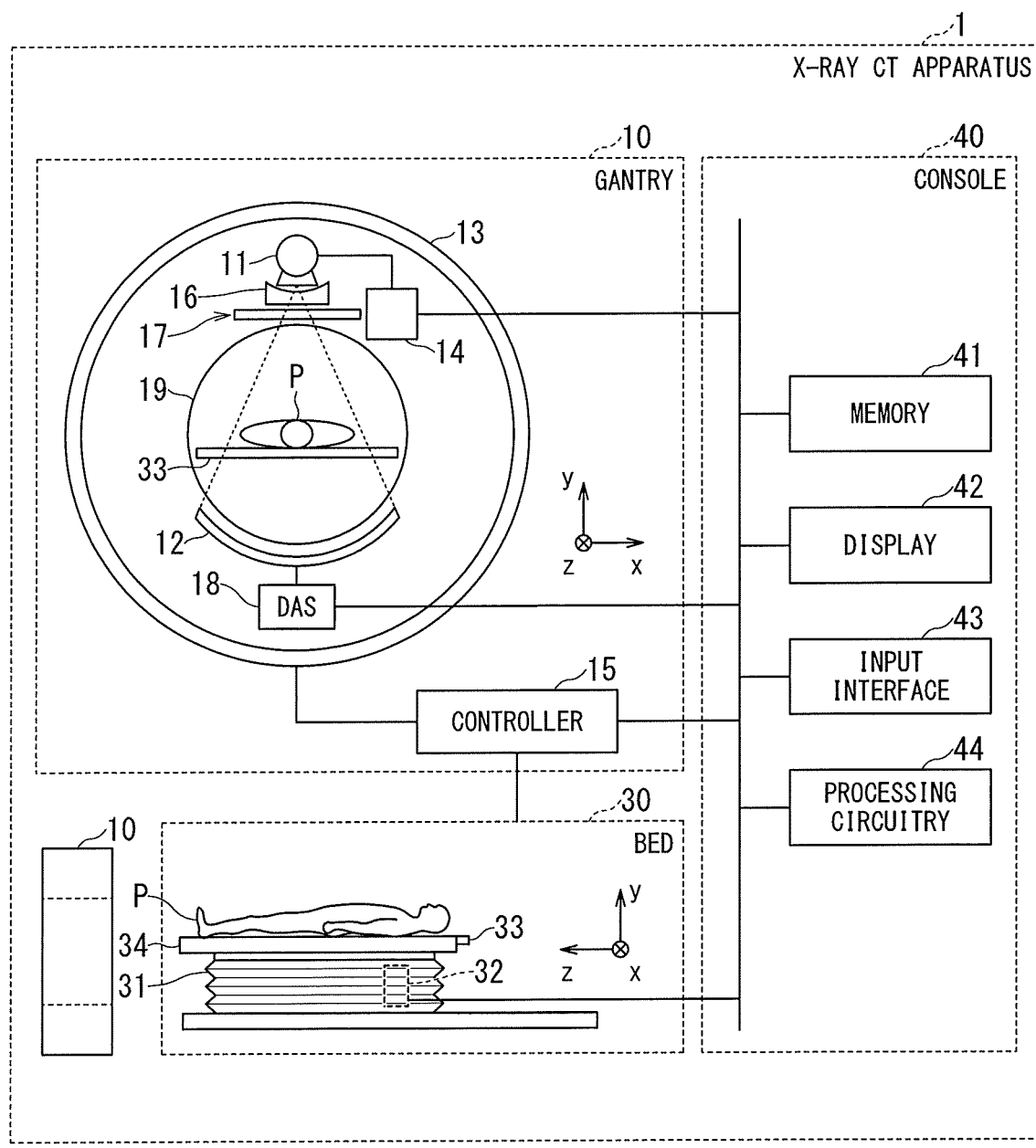
FIG. 1 is a schematic diagram showing a configuration of an X-ray CT apparatus including a medical image processing apparatus according to a first embodiment.
Figure 2:
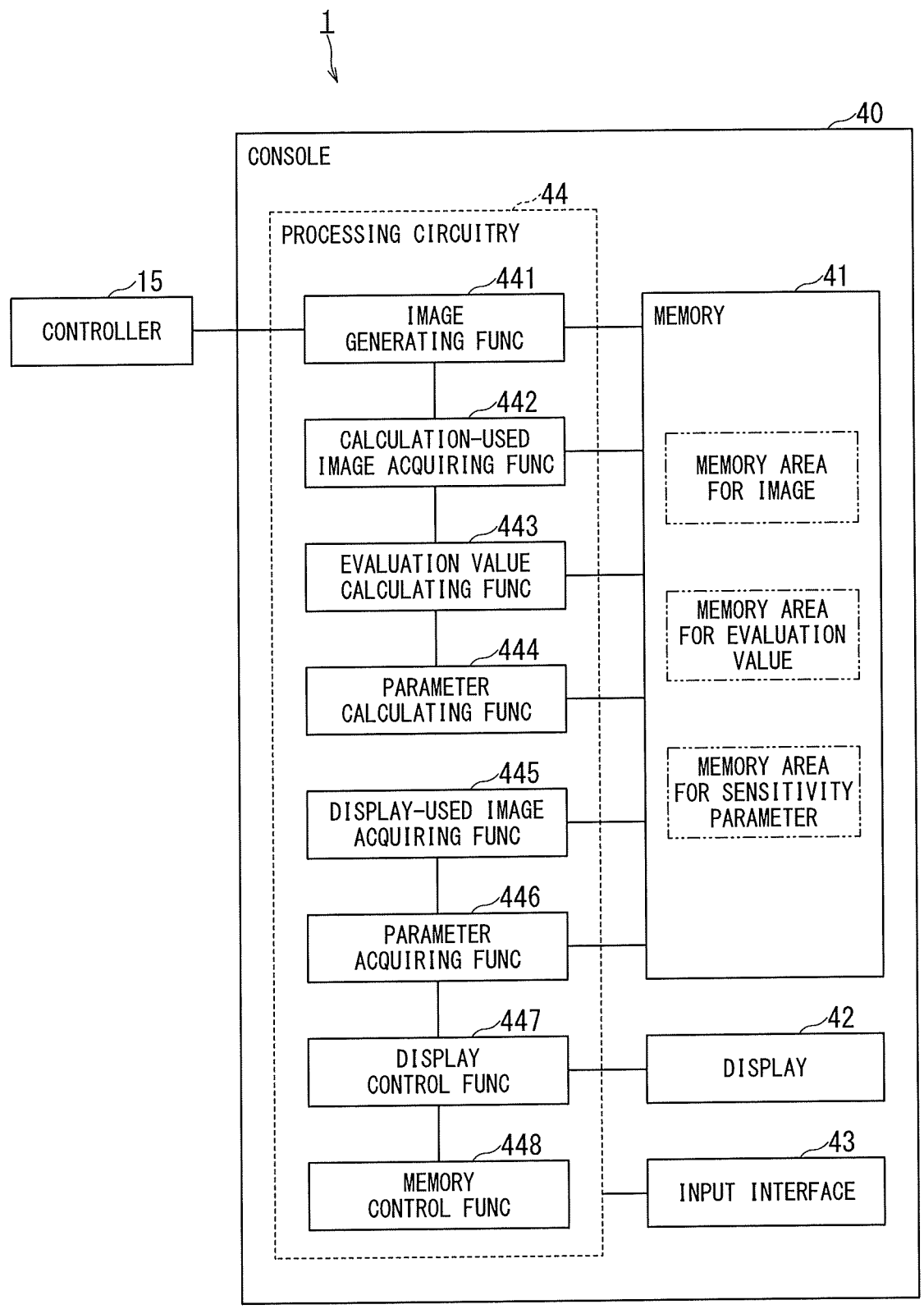
FIG. 2 is a block diagram showing a configuration and functions of the X-ray CT apparatus including the medical image processing apparatus according to the first embodiment.

FIG. 1 is a schematic diagram showing a configuration of an X-ray CT apparatus including a medical image processing apparatus according to a first embodiment. FIG. 2 is a block diagram showing a configuration and functions of the X-ray CT apparatus including the medical image processing apparatus according to the first embodiment.

FIG. 1 shows an X-ray CT apparatus. The X-ray CT apparatus 1 includes a gantry 10, a bed 30, and a medical image processing apparatus according to a first embodiment, that is, a console 40. The gantry 10 and the bed 30 are installed in an examination room. The gantry 10 acquires X-ray detection data (pure raw data) related to a subject (e.g., a patient) P placed on the bed 30. The console 40 generates raw data by pre-processing the detection data for views, and reconstructs CT image data by performing reconstruction processing on the raw data for display.

In FIG. 1, for convenience of explanation, multiple gantries 10 are drawn on the upper left and lower sides, but in the actual configuration, there is one gantry 10.

The gantry 10 includes an X-ray source (e.g., X-ray tube) 11, an X-ray detector 12, a rotating portion (for example, rotating frame) 13, an X-ray high-voltage device 14, a controller 15, a wedge 16, a collimator 17 and a data acquisition system (DAS) 18. The gantry 10 is an example of a gantry unit.

The X-ray tube 11 is provided in the rotating frame 13. The X-ray tube 11 is a vacuum tube which generates X-rays by radiating thermoelectrons from a cathode (filament) to an anode (target) with high voltage supplied from the X-ray high-voltage device 14. For example, the X-ray tube 11 includes a rotating anode type X-ray tube which generates X-rays by irradiating a rotating anode with thermoelectrons.

The present embodiments may be applied to a single-tube type X-ray CT apparatus or to a so-called multi-tube type X-ray CT apparatus in which pairs of an X-ray tube and an X-ray detector are mounted on a rotation ring. The X-ray source for generating X-rays is not limited to the X-ray tube 11. Instead of the X-ray tube 11, for instance, X-rays may be generated by the fifth generation type. The fifth generation type includes a focus coil for converging an electron beam generated from an electron gun, a deflection coil for electromagnetically deflecting the electron beam, and a target ring that encloses a half of the circumference of the patient P, and generates X-rays by being subjected to collision of the deflected electron beam. The X-ray tube 11 is an example of an X-ray irradiation unit.

The X-ray detector 12 is provided in the rotating frame 13 so as to face the X-ray tube 11. The X-ray detector 12 detects X-rays radiated from the X-ray tube 11 and outputs detection data corresponding to X-ray dose to the DAS 18 as an electric signal. The X-ray detector 12 includes, e.g., plural X-ray detection element lines configured by arraying plural X-ray detection elements in the channel direction along one circular arc such that the focus of the X-ray tube becomes the center of the array. For instance, the X-ray detector 12 has a structure in which X-ray detection element lines configured by arraying X-ray detection elements in the channel direction are arrayed in the slice direction (for example, row direction).

Further, the X-ray detector 12 is an indirect conversion type detector equipped with a grid, a scintillator array and an optical sensor array. The scintillator array includes multiple scintillators, and each scintillator has a scintillator crystal that outputs light with a photon dose corresponding to the incident X-ray dose. The grid is arranged on the surface on the X-ray incident side of the scintillator array, and has an X-ray shielding plate having a function of absorbing scattered X-rays. The grid is sometimes called a collimator (a one-dimensional collimator or a two-dimensional collimator). The photosensor array has a function of converting the light outputted from the scintillator into an electric signal corresponding to the light amount from the scintillator, and includes an optical sensor such as a photo multiplier tube (PMT), for example.

The X-ray detector 12 may be a direct conversion type detector having semiconductor elements which convert incident X-rays into electrical signals. The X-ray detector 12 is an example of an X-ray detection unit.

The rotating frame 13 supports the X-ray tube 11 and the X-ray detector 12 such that the X-ray tube 11 and the X-ray detector 12 face each other. The rotating frame 13 is an annular frame configured to integrally rotate the X-ray tube 11 and the X-ray detector 12 under the control of the controller 15 described below. The rotating frame 13 may further include and support the X-ray high-voltage device 14 and the DAS 18, in addition to the X-ray tube 11 and the X-ray detector 12. The rotating frame 13 is an example of a rotating portion.

In this manner, the X-ray CT apparatus 1 rotates the rotating frame 13, which makes the X-ray tube 11 and the X-ray detector 12 face each other with support, around the patient P so as to acquire detection data for multiple views, i.e., views of 360° of the entire surrounding of the patient P. The reconstruction method of the CT image data is not limited to the full scan reconstruction in which detection data of 360° are used. For instance, the X-ray CT apparatus 1 may adopt the half scan reconstruction in which CT image data is reconstructed on the basis of detection data of the half round (180°)+fan angle.

The X-ray high-voltage device 14 is provided on the rotating frame 13 or a non-rotating portion (for example, a fixed frame not shown) which rotatably supports the rotating frame 13. The X-ray high-voltage device 14 includes electric circuits such as a transformer and a rectifier. The X-ray high-voltage device 14 includes a high-voltage generator (not shown) having a function of generating a high voltage applied to the X-ray tube 11 under the control of the controller 15 described below and an X-ray controller (not shown) for controlling the output voltage according to X-rays radiated by the X-ray tube 11 under the control of the controller 15 described below. The high-voltage generator may be a transformer type or an inverter type. In FIG. 1, for convenience of explanation, the X-ray high-voltage device 14 is disposed at a position in a positive direction of the x-axis with respect to the X-ray tube 11. However, the X-ray high-voltage device 14 may be arranged at a position in a negative direction of the x-axis with respect to the X-ray tube 11.

The controller 15 includes processing circuitry, a memory and a driving mechanism such as a motor and an actuator. The configurations of the processing circuitry and the memory are respectively the same as those of the processing circuitry 44 and the memory 41 of the described below console 40, respectively, so duplicate description is omitted.

The controller 15 has a function of receiving an input signal from the input interface 43 described below of the console 40 or from an input interface (not shown) of the gantry 10, thereby controlling the operation of the gantry 10 and the bed 30. For example, on receiving the input signal, the controller 15 controls the rotation of the rotating frame 13, controls the gantry 10 so as to tilt the gantry 10, and controls the operation of the bed 30 and the table 33. The control of tilting the gantry 10 is achieved by the controller 15 that rotates the rotating frame 13 around the axis in parallel to the X-axis direction on the basis of tilt angle information inputted by the input interface of the gantry 10. The controller 15 may be provided in the gantry 10 or in the console 40. The controller 15 is an example of a control unit.

In addition, the controller 15 also controls the rotating angle of the X-ray tube 11, and the operation of the wedge 16 and the collimator 17 described below, on the basis of imaging conditions inputted from the input interface 43 of the console 40 or the input interface of the gantry 10.

The wedge 16 is provided on the rotating frame 13 so as to be disposed on the X-ray emission side of the X-ray tube 11. The wedge 16 is a filter for adjusting X-ray dose radiated from the X-ray tube 11 under the control of the controller 15. Specifically, the wedge 16 is a filter that transmits and attenuates the X-rays radiated from the X-ray tube 11 such that the X-rays radiated onto the patient P from the X-ray tube 11 have a predetermined distribution. For instance, the wedge 16 (for example, wedge filter, bow-tie filter) is a filter obtained by processing aluminum such that the aluminum has a predetermined target angle or a predetermined thickness.

The collimator 17 is also called a diaphragm or a slit, and is provided in the rotating frame 13 so as to be arranged on the X-ray emission side of the X-ray tube 11. The collimator 17 is, e.g., a lead plate for narrowing the irradiation range of the X-rays transmitted through the wedge 16 under the control of the controller 15, and forms an X-ray irradiation opening by a combination of plural lead blades and other components.

The DAS 18 is provided in the rotating frame 13. The DAS 18 includes an amplifier that performs amplification processing on electric signals outputted from the respective X-ray detection elements of the X-ray detector 12 under the control of the controller 15, and further includes an analog to digital (A/D) converter for converting the electric signals into digital signals under the control of the controller 15. The DAS 18 generates detection data subjected to the amplification processing and the digital conversion. The detection data for views generated by the DAS 18 are transferred to the console 40.

The detection data generated by the DAS 18 is transmitted from a transmitter to a receiver by optical communication and transferred to the console 40. The transmitter has a light emitting diode (LED) provided on the rotating frame 13. The receiver includes a photodiode provided on a fixed frame of the gantry 10. The detection data transmission method from the rotating frame 13 to the fixed frame of the gantry 10 is not limited to the optical communication described above, and any method may be adopted as long as it is a non-contact type data transmission.

The bed 30 includes a base 31, a bed driving device 32, a table 33, and a support frame 34. The bed 30 is a device for placing the patient P to be scanned and moving the patient P under the control of the controller 15.

The base 31 is a housing that supports the support frame 34 movably in the vertical direction (i.e., y-axis direction). The bed driving device 32 is a motor or an actuator that moves the table 33 with the patient P placed thereon in the longitudinal direction (i.e., z-axis direction) of the table 33. The table 33 provided on the upper surface of the support frame 34 is a plate having a shape capable of placing the patient P.

In addition to the table 33, the bed driving device 32 may move the support frame 34 in the longitudinal direction (i.e., z-axis direction) of the table 33. In addition, the bed driving device 32 may move the table 34 together with the base 31 of the bed 30. When the present invention is applied to the standing CT (i.e., CT in a standing position), it may be a method of moving the patient-moving-mechanism corresponding to the table 33. In the case of executing imaging that involves relative change of positional relationship between the table 33 and the imaging system of the gantry 10 such as helical scan imaging and scano imaging for positioning, the relative change of the positional relationship may be performed by driving the table 33, running the fixed frame of the gantry 10, or a combination of both.

In the embodiment, the rotation axis of the rotating frame 13 in the non-tilted state or the longitudinal direction of the table 33 of the bed 30 is defined as the z-axis direction, the axial direction orthogonal to the z-axis direction and horizontal to the floor surface is defined as the x-axis direction, and the axial direction orthogonal to the z-axis direction and perpendicular to the floor surface is defined as the y-axis direction.

The console 40 includes a memory 41, a display 42, an input interface 43, and processing circuitry 44. The console 40 is described as a separate body from the gantry 10, but the gantry 10 may include all or part of components of the console 40. In the following description, it is assumed that the console 40 executes all functions with a single console, but these functions may be executed by multiple consoles. The console 40 is an example of a medical image processing apparatus.

The memory 41 is configured by a random access memory (RAM), a semiconductor memory element such as a flash memory, a hard disk, an optical disk, or the like, for example. The memory 41 may be configured by a portable medium such as a universal serial bus (USB) memory and a digital video disk (DVD). The memory 41 stores various processing programs used in the processing circuitry 44 (including an operating system (OS) in addition to application programs) and data necessary for executing the programs. The OS can also include a graphic user interface (GUI). According to the GUI, graphics are frequently used for displaying information on the display 42 for the operator, and basic operations are performed by the input interface 43.

The memory 41 stores, for example, detection data before preprocessing, raw data after preprocessing and before reconstruction, and CT image data after reconstruction based on the raw data. The pre-processing means at least one of logarithmic conversion processing, offset correction processing, sensitivity correction processing between channels, beam hardening processing, and the like for detection data. Alternatively, the detection data, the raw data, or the CT image data may be stored in a cloud server in response to a request from the X-ray CT apparatus 1. The cloud server is connected to the X-ray CT apparatus 1 via a communication network such as the Internet.

Further, the memory 41 has at least a memory area for image, a memory area for evaluation value and a memory area for sensitivity parameter (shown in FIG. 2). The memory area for image stores the CT image data as medical image data. The memory area for evaluation value stores an evaluation value to be described later. The memory area for sensitivity parameter stores a sensitivity parameter described later. The memory 41 is an example of a storage.

The display 42 displays various types of information. For instance, the display 42 outputs the medical image data generated by the processing circuitry 44 and/or the GUI for receiving various operations from a user. The display 42 is, e.g., a liquid crystal display, a cathode ray tube (CRT) display, or an organic light emitting diode (OLED) display. The display 42 may be provided in the gantry 10. Further, the display 42 may be a desktop type, or may be configured by a tablet terminal or the like capable of wireless communication with the console 40. The display 42 is an example of a display unit.

The input interface 43 includes an input device which is operated by an operator such as an engineer, and an input circuit which inputs a signal from the input device. The input device is realized by a mouse, a keyboard, a trackball, a switch, a button, a joystick, a touch pad, a touch screen, a non-contact input circuit, a voice input circuit, and the like. The touch pad performs an input operation by touching an operation surface. The touch screen is formed by unifying a display screen and a touch pad. The non-contact input circuit uses an optical sensor. When the input device accepts an input operation from the operator, the input circuit generates an electrical signal corresponding to the input operation and outputs it to the processing circuitry 44. The input interface 43 may be provided in the gantry 10. Further, the input interface 43 may be configured by a tablet terminal or the like capable of wireless communication with the console 40. The input interface 43 is an example of an input unit.

It should be noted that the console 40 may be provided with a network interface (not shown). The network interface is configured by a connector adapted to a parallel connection specification or a serial connection specification. When the X-ray CT apparatus 1 is provided on a medical image system, the network interface transmits/receives information to/from an external apparatus on the network. For example, the network interface receives an examination order related to the CT examination from the external apparatus under the control of the processing circuitry 44. Further, the network interface transmits the detection data acquired by the X-ray CT apparatus 1 and the generated raw data or CT image data to the external apparatus.

The processing circuitry 44 controls the overall operation of the X-ray CT apparatus 1. The processing circuitry 44 may be a dedicated or general-purpose central processing unit (CPU), a microprocessor unit (MPU), or a graphics processing unit (GPU). The processing circuitry 44 may be an ASIC, a programmable logic device, or the like. An example of the programmable logic device is a simple programmable logic device (SPLD), a complex programmable logic device (CPLD), a field programmable gate array (FPGA), or the like.

Further, the processing circuitry 44 may be configured by a single circuit or a combination of multiple independent processing circuit elements. In the latter case, multiple memories may be provided for the respective processing circuit elements, or a single memory may store a program corresponding to the functions of the multiple processing circuit elements. The processing circuitry 44 is an example of a processing unit.

The processing circuitry 44 executes a computer program stored in a non-transitory computer medium such as the memory 41 or a memory in the processing circuitry 44. Thereby, the processing circuitry 44 realizes an image generating function 441, a calculation-used image acquiring function 442, an evaluation value calculating function 443, a parameter calculating function 444, a display-used image acquiring function 445, a parameter acquiring function 446, a display control function 447 and a memory control function 448, as shown in FIG. 2. All or part of the functions 441 to 448 are not limited to the case where they are realized by executing the computer program of the console 40. All or part of the functions 441 to 448 may be provided in the console 40 as functions of a circuit such as an ASIC. All or part of the functions 441 to 448 may be realized not only by the console 40 but also by the controller 15.

The image generating function 441 includes a function of executing a CT scan by controlling the X-ray tube 11 and the X-ray detector 12 via the controller 15 according to a preset scan condition, thereby acquiring detection data for multiple views from the controller 15. For example, the scan condition includes a tube current mA, a tube voltage kV, an X-ray intensity control condition (X-ray modulation condition), a rotation speed of the X-ray tube 11 (or the rotating frame 13), and the like regarding irradiation X-rays.

Further, the image generating function 441 includes a function of acquiring raw data for multiple views by performing preprocessing on the acquired detection data for multiple views, and a function of generating CT image data as medical image data by image reconstruction processing based on the raw data for multiple views after preprocessing. The image generating function 441 may include a function of storing the CT image data in the memory 41, a function of displaying the CT image data on the display 42 as a CT image, and a function of transmitting the CT image data to an external apparatus via a network interface (not shown). The image generating function 441 is an example of an image generating unit.

The calculation-used image acquiring function 442 includes a function of acquiring, from the multiple CT image data stored in the memory 41, multiple CT image data (hereinafter referred to as "calculation-used CT image data") for calculating an evaluation value and a sensitivity parameter, which will be described later. The calculation-used image acquiring function 442 may acquire all the multiple CT image data stored in the memory 41 as the calculation-used CT image data. Alternatively, the function 442 may acquire a part of the multiple CT image data stored in the memory 41 as the calculation-used CT image data. The calculation-used image acquiring function 442 is an example of an image acquiring unit or a calculation-used image acquiring unit.

The evaluation value calculating function 443 includes a function of calculating evaluation values of the multiple calculation-used CT image data acquired by the calculation-used image acquiring function 442, and a function of storing each calculation-used CT image data in the memory 41 in association with the corresponding evaluation value. The evaluation value is a value indicating the display priority when each calculation-used CT image data is compared with other calculation-used CT image data. When the evaluation value is associated with each calculation-used CT image data, a table in which the evaluation value is associated with each calculation-used CT image data can be created and held. Alternatively, an evaluation value can be attached to a digital imaging and communications in medicine (DICOM) file related to each calculation-used CT image data. The evaluation value calculating function 443 is an example of an evaluation value calculating unit.

First, the evaluation value calculating function 443 estimates an attention region (for example, a clinically important region or a lesion site), and calculates an evaluation value of each calculation-used CT image data according to a distance from the attention region. In this case, the evaluation value calculating function 443 performs the estimation of the attention region and the calculation of the evaluation value using the following evaluation items [1] to [7]. Second, the evaluation value calculating function 443 estimates a state where partial re-imaging is necessary, and calculates an evaluation value of each calculation-used CT image data according to the state. In this case, the evaluation value calculating function 443 performs the estimation of a re-imaging position and the calculation of the evaluation value using the following evaluation items [8] and [9]. For example, the evaluation value calculating function 443 estimates the state of the patient P at the time of scanning, and calculates the evaluation value of each calculation-used CT image data according to the state. In this case, the evaluation value calculating function 443 performs the estimation of the state of the patient P and the calculation of the evaluation value using the next evaluation item [8].

[1] Imaging Conditions (Helical Pitch, Tube Current, Exposure Dose, etc.)

The evaluation value calculating function 443 estimates a z-position where an attention region such as a lesion site exists based on a change in imaging conditions, and calculates an evaluation value according to a distance in the z-axis direction from the estimated z-position. For example, when a helical scan is performed in which the helical pitch as the imaging condition changes along the z-axis direction, a high evaluation value is set for calculation-used CT image data corresponding to a z-position where the helical pitch is short. On the other hand, the evaluation value is set low for calculation-used CT image data corresponding to a z-position where the helical pitch is long. This is because it can be estimated that the z-position with a shorter helical pitch is closer to the attention region.

Figure 3:
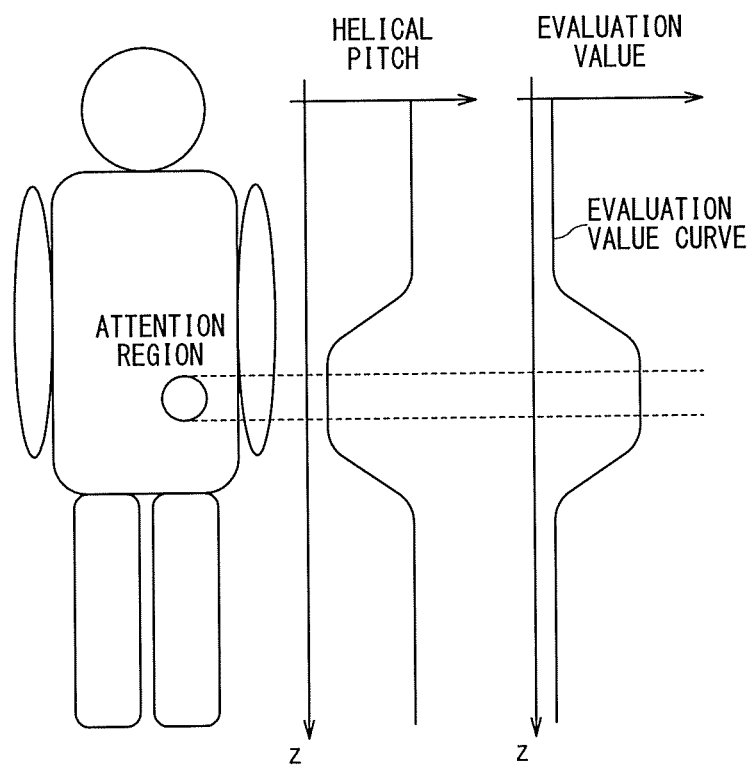
FIG. 3 is a diagram showing a relationship between a helical pitch and an evaluation value in the X-ray CT apparatus including the medical image processing apparatus according to the first embodiment.

FIG. 3 is a diagram showing a relationship between the helical pitch and the evaluation value.

As shown in FIG. 3, a helical scan is performed in which the helical pitch changes along the z-axis direction, and it is assumed that a z-position having a short helical pitch exists in the vicinity of the abdomen. In this case, the evaluation value calculating function 443 determines that there is a high possibility that the attention region exists near a z-position where the helical pitch is short, and sets an evaluation value near the z-position higher than evaluation values at other z-positions.

For example, when a scan in which the tube current as the imaging condition changes along the z-axis direction is performed, the evaluation value calculating function 443 sets the evaluation value near a z-position where the tube current is large, as a value larger than evaluation values of other z-positions. For example, when a scan is performed in which the exposure dose as the imaging condition changes along the z-axis direction, the evaluation value calculating function 443 sets the evaluation value near a z-position where the exposure dose is large, as a value larger than evaluation values of other z-positions. This is because it is assumed that an operator such as an engineer is going to visually recognize whether or not the calculation-used CT image data near the z-position corresponding to shorter helical pitch, large tube current or larger exposure dose has an image quality commensurate with the exposure dose etc.

For example, when a scan is performed in which the tube current as the imaging condition changes along the z-axis direction, the evaluation value calculating function 443 sets the evaluation value near the z-position where the tube current is small, as a value larger than evaluation values of other z-positions. This is because it is assumed that the operator is going to visually recognize whether or not the calculation-used CT image data near the z-position corresponding to smaller tube current has sufficient image quality when the tube current is set small to reduce exposure. For example, when a scan in which the tube current as the imaging condition changes along the z-axis direction is executed, the evaluation value calculating function 443 sets the evaluation value near the z-position where the difference from the tube current when a scan that does not change along the z-axis direction is executed is greater than a threshold value, as a value larger than evaluation values of other z-positions. This is because it is assumed that the operator is going to visually recognize whether or not the calculation-used CT image data near the z-position corresponding to excessive or excessive tube current has sufficient image quality commensurate with the tube current when the tube current is set large or small.

[2] Region of Interest (ROI) Set in CT Image Data

The evaluation value calculating function 443 estimates a z-position where an attention region such as a lesion site exists based on the z-position of the ROI set in at least one of the multiple CT image data, and calculates an evaluation value according to a distance in the z-axis direction from the estimated z-position. This is because the ROI (including the annotation ROI) is supposed to be set around the attention region, and therefore it is assumed that the operator visually recognizes the periphery of the attention region using the calculation-used CT image data of the z-position including the ROI.

In the present embodiments, the ROI may be an ROI set in display-used CT image data to be described later, or an ROI set in other image data (for example, scano image data) in which the z-position is associated with the display CT image data.

[3] Description of Examination Order or Electronic Medical Record

The evaluation value calculating function 443 estimates a z-position where an attention region such as a lesion site exists based on a description of an electronic medical record or the like, and calculates an evaluation value according to a distance in the z-axis direction from the estimated z-position. This is because it is assumed that the operator visually recognizes the periphery of the attention region, using the calculation-used CT image data of the z-position including the attention region described in the electronic medical record or the like. It should be noted that examples of the attention region are the following attention regions [a] to [e].

[a] Imaging target region included in examination order

[b] Region estimated from contents of the comment column of electronic medical record (for example, region "liver" estimated from comment "suspected cirrhosis")

[c] Past imaging region or Medical interpretation region

[d] Diagnostic region set for each disease (determinable based on diagnostic guidelines, etc.)

[e] Region related to region determined based on any of attention regions [a] to [d]

Each of the above attention regions [a] to [d] may be based on a position and a range directly designated by the operator on the displayed CT image using the input interface 43, or may be extracted using an existing algorithm which automatically extracts an anatomical position and range. The attention region [e], that is, an example of the related region is a region that are highly likely to be affected by disease, the region including a region having a high possibility of metastasis from the attention region [a] to [d] and a region having a large change in composition. The related region may be registered in advance in relation to any of the attention regions [a] to [d].

[4] Result Value by Analysis Algorithm

The evaluation value calculating function 443 estimates a z-position where an attention region such as a lesion site exists based on a result value obtained by an analysis algorithm, and calculates an evaluation value according to a distance in the z-axis direction from the estimated z-position. This is because it is assumed that the operator visually recognizes whether or not there is an abnormality, using the calculation-used CT image data of the z-position where there is a possibility of the attention region by the analysis algorithm. The result value obtained by the analysis algorithm includes the following result value [f] or [g].

[f] Analysis value indicating possibility of lesion by a lesion site extraction algorithm

[g] Analysis value indicating probability of corresponding region in algorithm for extracting anatomical position and range

[5] Difference Value from Past Image, Typical Image and Previous/Next Image

The evaluation value calculating function 443 estimates a z-position where an attention region such as a lesion site exists based on a difference value from a past image, and calculates an evaluation value according to a distance in the z-axis direction from the z-position. This is because, in the follow-up observation or the like, it is assumed that the operator visually recognizes the calculation-used CT image data of the z-position including a region having a large difference from the past image.

The evaluation value calculating function 443 estimates a z-position where an attention region such as a lesion site exists based on a difference value from the typical image, and calculates an evaluation value according to the distance in the z-axis direction from the z-position. This is because, in the follow-up observation or the like, it is assumed that the operator visually recognizes the calculation-used CT image data of the z-position including a region having a large difference from the typical image. The typical image means a typical model such as Atlas which shows the internal structure of the entire human body or the structure of each part. The typical model may be owned in each hospital. It should be noted that the evaluation value calculating function 443 may be based on a result value obtained by an analysis algorithm when estimating a z-position where the attention region such as a lesion site exists based on a difference value from the typical image.

The evaluation value calculating function 443 estimates a z-position where an attention region such as a lesion site exists based on a difference value from a previous/next image, and calculates an evaluation value according to a distance in the z-axis direction from the z-position. This is because, in the follow-up observation or the like, it is assumed that the operator visually recognizes the calculation-used CT image data of the z-position including a region having a large difference from the previous/next image. The previous/next image means a previous image and/or a next image of each image along the z-axis direction.

It should be noted that the difference processing with the past image, the typical image, and the previous/next image may be performed on the whole image, and may be performed partially.

[6] Past Observation Time

The evaluation value calculating function 443 estimates a z-position where an attention region such as a lesion site exists based on a past observation time, and calculates an evaluation value according to a distance in the z-axis direction from the estimated z-position. This is because it is assumed that the operator attentively visually recognizes, when the operator diagnoses a similar image in the past, the calculation-used CT image data having the same z-position as the image observed over time, because the similar image should be viewed with the same attention.

[7] Reconstruction Condition

The evaluation value calculating function 443 estimates a z-position where an attention region such as a lesion site exists based on a reconstruction condition, for example, a slice interval of multiple reconstructed CT images, and calculates an evaluation value according to a distance in the z-axis direction from the estimated z-position. This is because it is assumed that the slice interval between the multiple CT image data should be small around the attention region, and the operator visually recognizes the periphery of the attention region, using the calculation-used CT image data of the z-position where the slice interval between multiple reconstructed CT images is small. The reconstruction condition is not limited to the slice interval of the multiple CT images. The reconstruction condition may be, for example, a resolution of each CT image, a display field of view (DFOV), or the like. The DFOV represents the image size, and means the length of one side of a rectangular image, or the diameter of a circular image.

[8] Patient Body Movement and Degree of Arrhythmia

The evaluation value calculating function 443 estimates the degree of body movement or arrhythmia of the patient P, and calculates an evaluation value according to a distance in the z-axis direction from a z-position where the body motion or arrhythmia of the patient P shows an abnormal value. This is because it is assumed that when body movement or arrhythmia of the patient P occurs during the scan, a motion artifact occurs in the CT image data, so the operator visually recognizes the calculation-used CT image data of the z-position of the artifact to request a partial re-imaging.

[9] Lack of Data and Artifact

The evaluation value calculating function 443 estimates a z-position where data is lost due to discharge of the X-ray tube 11 during scanning, and calculates an evaluation value according to a distance in the z-axis direction from the estimated z-position. This is because it is assumed that when the discharge of the X-ray tube 11 during scanning occurs, data loss occurs, so the operator visually recognizes the calculation-used CT image data of the z-position of the data loss to request a partial re-imaging.

The evaluation value calculating function 443 estimates a z-position where a part with an artifact or a part where noise easily exists, and calculates an evaluation value according to a distance in the z-axis direction from the estimated z-position. This is because it is assumed that the operator visually recognizes the calculation-used CT image data of the z-position of a region where the artifact is present or where noise is likely to be picked up to request a partial re-imaging. The region may be a preset position, or may be obtained from the amount of noise obtained from each calculation-used CT image data.

The evaluation value calculating function 443 may calculate an evaluation value using any one of the evaluation items [1] to [9], or may calculate some of the evaluation items [1] to [9] as evaluation value elements and combine them to calculate one evaluation value. In the latter case, the evaluation value calculating function 443 may calculate a single evaluation value by simple averaging or simple addition of evaluation value elements, or may calculate one evaluation value by weighted average or weighted addition of evaluation value elements. For example, the weighting is to make the weight of the evaluation value element, which is estimated to be more important to the operator among evaluation value elements, heavier than the other evaluation value elements.

The parameter calculating function 444 includes a function of calculating a sensitivity parameter indicating the forwarding/reversing number of multiple displayed CT image data of the multiple CT image data to be displayed (hereinafter referred to as "display-used CT image data") for an operation amount, based on the evaluation value calculated by the evaluation value calculating function 443, and a function of storing the sensitivity parameter of each display-used CT image data in the memory 41 in association with the corresponding calculation CT image data. The forwarding/reversing number means the number of images to be forwarded/reversed from image data at a specific position to image data at another position among multiple image data arranged along positions (for example, z-positions). Alternatively, the forwarding/reversing number means the number of images to be forwarded/reversed from image data at a specific imaging time to image data at another imaging time among multiple image data arranged along imaging times. The parameter calculating function 444 is an example of a parameter calculating unit.

Figure 4:
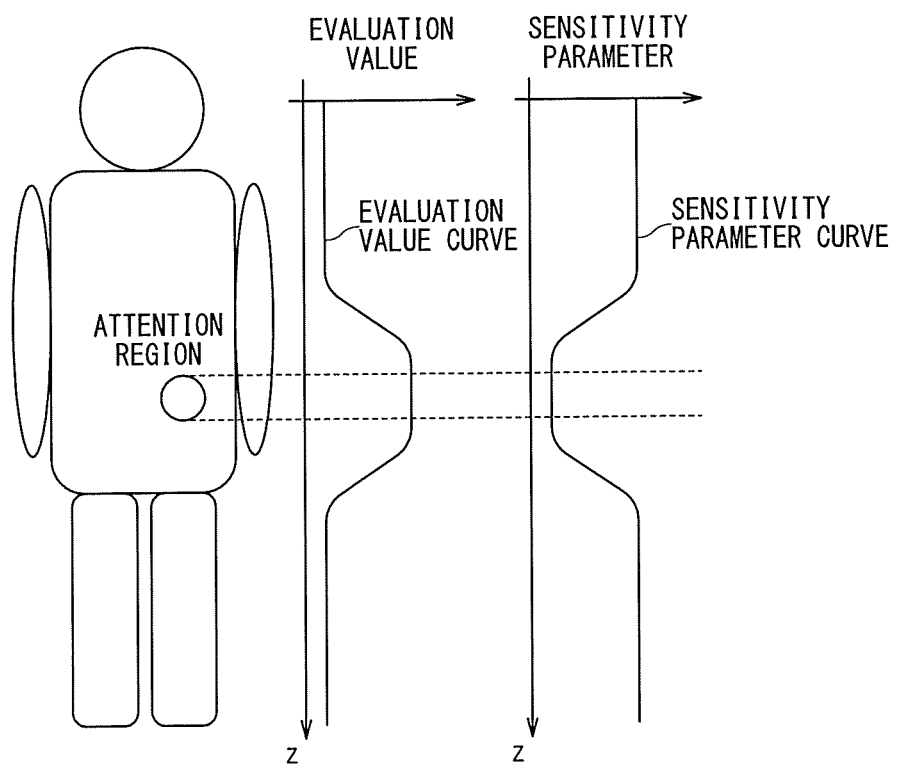
FIG. 4 is a diagram showing a relationship between an evaluation value and a sensitivity parameter in the X-ray CT apparatus including the medical image processing apparatus according to the first embodiment.

FIG. 4 is a diagram showing a relationship between the evaluation value and the sensitivity parameter.

As shown in FIG. 4, it is assumed that there is an evaluation value curve in which an evaluation value is set high near the abdomen. In this case, the parameter calculating function 444 calculates the sensitivity parameters as the sensitivity parameter curve so that a sensitivity parameter near the abdomen is set lower (duller) than other z-positions. There is a high possibility that the attention region is included near the z-position where the evaluation value is set high.

Figure 5:
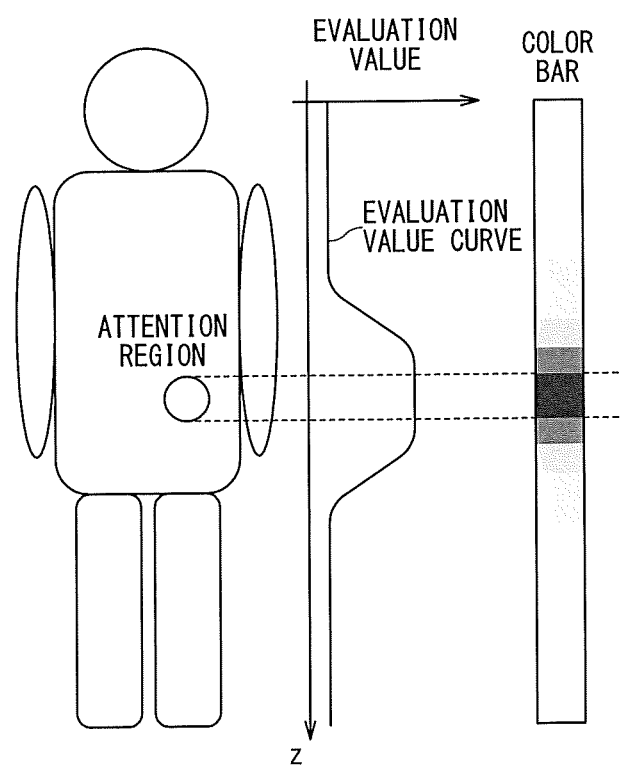
FIG. 5 is a diagram showing a relationship between an evaluation value and a color bar indicating a sensitivity parameter in the X-ray CT apparatus including the medical image processing apparatus according to the first embodiment.

The parameter calculating function 444 may display the sensitivity parameter curve of FIG. 4. The parameter calculating function 444 may display a color bar indicating the sensitivity parameters in FIG. 4 in color (hue, brightness, saturation) on the display 42 (shown in FIG. 5). The parameter calculating function 444 may display the sensitivity parameter curve on the scano image. Furthermore, it may be configured such that the operator can manually adjust the evaluation value or the evaluation value curve once calculated, as necessary.

Figure 6:
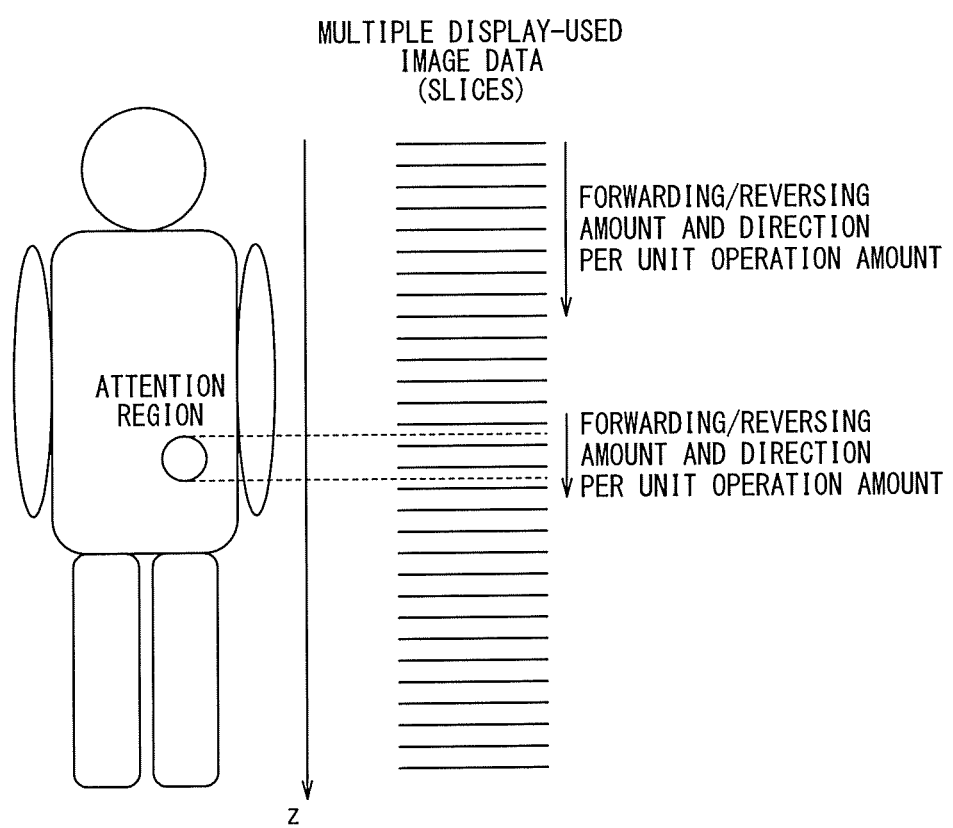
FIG. 6 is a diagram for explaining a sensitivity parameter in the X-ray CT apparatus including the medical image processing apparatus according to the first embodiment.

FIG. 6 is a diagram for explaining the sensitivity parameter.

The sensitivity parameter means the forwarding/reversing number of displayed images with respect to the unit operation amount of the input interface 43. For example, "the sensitivity parameter is large" means that the forwarding/reversing number of displayed images with respect to the unit operation amount of the trackball is large, and "Sensitivity parameter is small" means that the forwarding/reversing number of displayed images with respect to the unit operation amount of the trackball is small.

The parameter calculating function 444 increases the forwarding/reversing number of displayed images with a large sensitivity parameter at the z-position where the evaluation value is low with respect to the unit operation amount of the input interface 43. That is, at the z-position where the evaluation value is low, the forwarding/reversing number of displayed images per unit time increases, and as a result, the forwarding/reversing speed of displayed images increases. On the other hand, the parameter calculating function 444 reduces the forwarding/reversing number of displayed images with a small sensitivity parameter at the z-position where the evaluation value is high with respect to the unit operation amount of the input interface 43. That is, at the z-position where the evaluation value is high, the forwarding/reversing number of displayed images per unit time decreases, and as a result, the forwarding/reversing speed of displayed image decreases.

Returning to the description of FIG. 2, the display-used image acquiring function 445 includes a function of acquiring multiple display-used CT image data from the memory 41. Here, the multiple display-used CT image data may be the same as the multiple calculation CT image data described above (shown in FIG. 7A), or they may be extracted (shown in FIG. 7B). The display-used image acquiring function 445 is an example of a display-used image acquiring unit.

The parameter acquiring function 446 includes a function of acquiring, from the memory 41, sensitivity parameters of the multiple display-used CT image data calculated by the parameter calculating function 444. The parameter acquiring function 446 is an example of a parameter acquiring unit.

The display control function 447 controls the multiple display-used CT image data acquired by the display-used image acquiring function 445 on the basis of the evaluation value corresponding to each CT image data of the multiple calculation-used CT image data acquired by the calculation-used image acquiring function 442, thereby controlling the forwarding/reversing number or forwarding/reversing speed of displayed images for the operation amount. Specifically, the display control function 447 includes a function of displaying the multiple display-used CT image data on the display 42 as CT images on the basis of the sensitivity parameter, acquired by the parameter acquiring function 446, based on the evaluation value. The display control function 447 is an example of a display control unit.

The memory control function 448 includes a function of calculating an interval to be stored of the multiple display-used CT image data based on the evaluation value calculated by the evaluation value calculating function 443, thereby storing a part of the multiple display-used CT image data in the memory 41 according to the interval to be stored. The memory control function 448 is an example of a memory control unit.

FIG. 8 is a diagram showing a relationship between the evaluation value and the interval to be stored.

It is assumed that there is an evaluation value curve with a high evaluation value set near the abdomen. In this case, the memory control function 448 determines that there is a high possibility that the attention is included near the z-position where the evaluation value is set high, thereby sets the interval to be stored smaller than other z-positions.

A general image storage tool is possible to store multiple CT image data within a specific range in the z-axis direction. Thereby, it is possible to store all the multiple slice image data in a regular interval. In contrast to such an image storage tool, the memory control function 448 is possible to store the multiple slice image data within the specific range so that an interval to be stored is smaller near a slice having higher importance for the operator on the basis of the evaluation value. Thus, it is possible to increase the number of important slices to be stored while reducing the number of less important slices to be stored. Thereby, it is easy to observe the image and it is possible to avoid storing an unnecessary image.

The operation of the functions 441 to 447 will be described later with reference to FIGS. 9 and 10.

Each of FIGS. 9 and 10 is a diagram showing the operation of the X-ray CT apparatus 1 as a flowchart. In FIGS. 9 and 10, reference numerals formed by adding numbers to "ST" indicate steps in the flowchart.

First of all, in FIG. 9, the operator operates the input interface 43 in a state where a patient P scheduled to perform a CT scan is placed on the table 33. Thus the image generating function 441 controls the X-ray tube 11 and the X-ray detector 12 and the like via the controller 15 in accordance with a scan condition set in advance, thereby performs the CT scan such as a volume scan (also called "conventional scan") or a helical scan (step ST1). The image generating function 441 acquires detection data for views from the controller 15 by the CT scan. It should be noted that description of the pre-scan (also called "scano imaging" or "scout imaging") performed prior to the execution of the CT scan in step ST1 is omitted.

In the present embodiments, the volume scan means a non-helical scan and means a scan executed without changing the relative positions of the gantry 10 and the bed 30. The helical scan means a scan executed while moving the table 33 of the bed 30 in the z-axis direction with respect to the gantry 10. Alternatively, the helical scan means a scan that is executed while moving the gantry 10 in the z-axis direction with respect to the bed 30.

The image generating function 441 performs preprocessing on the detection data for views acquired by the CT scan in step ST1, thereby acquires raw data for views (step ST2).

The image generating function 441 generates multiple CT image data by image reconstruction processing based on the raw data for views after the preprocessing in step ST2 (step ST3). Each of the multiple CT image data is an example of the medical image data. The image generating function 441 stores each CT image data generated in step ST3 in the memory 41 (step ST4). The image generating function 441 may display each CT image data on the display 42 as a CT image, or may transmit each CT image data to an external apparatus via a network interface (not shown).

The calculation-used image acquiring function 442 acquires multiple calculation-used CT image data from the multiple CT image data generated in step ST3 and stored in the memory 41 (step ST5). In step ST5, the calculation-used image acquiring function 442 may acquire all the multiple CT image data stored in the memory 41 as the multiple calculation-used CT image data, or may acquire a part of the multiple CT image data as the multiple calculation-used CT image data.

The evaluation value calculating function 443 calculates an evaluation value of each calculation-used CT image data acquired in step ST5 (step ST6). The evaluation value calculating function 443 stores the evaluation value of each calculation-used CT image data calculated in step ST5 in the memory 41 in association with the corresponding calculation-used CT image data (step ST7).

The parameter calculating function 444 calculates sensitivity parameters of the multiple display-used CT image data based on the evaluation value calculated in step ST6 (step ST8). The parameter calculating function 444 stores the sensitivity parameter of each display-used CT image data calculated in step ST8 in the memory 41 in association with the corresponding calculation-used CT image data (step ST9).

By the operation of steps ST1 to ST9 shown in FIG. 9, the console 40 is possible to calculate a sensitivity parameter corresponding to each calculation-used CT image data, and to store the multiple sensitivity parameters together with the multiple calculation-used CT image data.

Proceeding to the description of FIG. 10, the display-used image acquiring function 445 acquires multiple display-used CT image data from the multiple CT image data stored in step ST4 from the memory 41 (step ST11). The parameter acquiring function 446 acquires the sensitivity parameter corresponding to each calculation-used CT image data stored in step ST9 from the memory 41 (step ST12).

The display control function 447 displays n-th display-used CT image data of the multiple display-used CT image data acquired in step ST11 as a displayed image to the display 42 (step ST13). The display control function 447 receives an operation on the n-th display CT image data displayed in step ST13 (step ST14). The display control function 447 forwards (or reverses) the displayed image from the n-th display-used CT image data to m-th display-used CT image data according to the operation amount in step ST14 and the sensitivity parameter acquired in step ST12, the m-th display-used CT image data being of the multiple display-used CT image data. Thereby, the display control function 447 updates a displayed image (step ST15).

As described above, the X-ray CT apparatus 1 is possible to efficiently acquire desired display CT image data from among the multiple display CT image data, and represent it to the operator, thereby improve diagnostic efficiency.

2. Medical Image Processing Apparatus According to Second Embodiment

A medical image processing apparatus according to a second embodiment is configured as a separate body from the medical image diagnostic apparatus.

FIG. 11 is a block diagram showing a configuration and functions of a medical image processing apparatus according to a second embodiment.

FIG. 11 shows a medical image processing apparatus 70 according to a second embodiment. The medical image processing apparatus 70 is a medical image managing apparatus (image server), a workstation, a medical interpretation terminal, or the like, and is provided on a medical image system connected via a network. In this case, the medical image processing apparatus 70 includes a network interface (not shown). The network interface is configured by a connector adapted to a parallel connection specification or a serial connection specification. When the medical image processing apparatus 70 is provided on the medical image system, the network interface transmits/receives information to/from an external apparatus on the network. For example, the network interface receives medical image data such as CT image data from an external apparatus under the control of processing circuitry 74. The medical image processing apparatus 70 may be an offline apparatus.

The medical image processing apparatus 70 includes a memory 71, a display 72, an input interface 73, and processing circuitry 74. The memory 71, the display 72, the input interface 73, and the processing circuitry 74 have the same configuration as that of the memory 41, the display 42, the input interface 43, and the processing circuitry 44 shown in FIGS. 1 and 2, so their explanations are omitted.

The processing circuitry 74 executes a computer program stored in a non-transitory computer medium such as the memory 71 or a memory in the processing circuitry 74. Thereby, the processing circuitry 74 realizes a calculation-used image acquiring function 742, an evaluation value calculating function 743, a parameter calculating function 744, a display-used image acquiring function 745, a parameter acquiring function 746, a display control function 747 and a memory control function 748. All or part of the functions 742 to 748 are not limited to the case where they are realized by executing the computer program of the medical image processing apparatus 70. All or part of the functions 742 to 748 may be provided in the medical image processing apparatus 70 as functions of a circuit such as an ASIC. Further, the sensitivity parameter calculation process may be calculated in advance by the medical image diagnostic apparatus, the medical image managing apparatus, or the like that generates medical image data, and thus the functions 742 to 744 are not essential components.

The calculation-used image acquiring function 742 includes a function equivalent to the calculation-used image acquiring function 442 shown in FIG. 2. In addition, the calculation-used image acquiring function 742 includes a function of acquiring not only the multiple calculation-used CT image data but also multiple medical image data (hereinafter referred to as "calculation-used image data") for calculating an evaluation value and a sensitivity parameter described later.

The calculation-used image acquiring function 742 may acquire multiple calculation-used image data as types of medical image data different from the multiple display-used image data. In this case, it is assumed that the multiple calculation-used image data is associated with multiple different medical image data such as alignment. For example, the multiple different medical image data may be multiple past medical image data acquired by imaging the same part, may be different types of functional image data as in the case of perfusion image data or the like, or may be multiple image data acquired by imaging with a medical image diagnostic apparatus different from the medical image diagnostic apparatus that generates display-used image data. The calculation-used image acquiring function 742 is an example of an image acquiring unit or a calculation-used image acquiring unit.

The evaluation value calculating function 743 includes a function equivalent to evaluation value calculating function 443 shown in FIG. 2. The evaluation value calculating function 743 is an example of an evaluation value calculating unit.

Further, the evaluation value calculating function 743 performs estimation of an attention region and calculation of an evaluation value by the following evaluation item [10] in addition to the above evaluation items [1] to [9].

[10] Pixel Value of Image

The evaluation value calculating function 743 calculates a distance from a z-position of the lesion site estimated based on pixel values of the medical image data as an evaluation value. This is because it is assumed that, in an image such as a functional image typified by a PET image, the importance for the operator changes depending on the level of the pixel values. For example, in the PET image, a portion showing high pixel values, that is high standardized uptake values (SUV), means that the corresponding tissue is actively taking up a substance. The presence of a malignant tumor is suspected in a portion where the SUV values are abnormally high compared to the surrounding area. On the other hand, if it is lower than the surrounding area, the tissue may not function. Based on a value acquired from such a functional image, an evaluation value may be calculated.

The evaluation value calculating function 743 may calculate an evaluation value using any one of the above evaluation items [1] to [10], or may calculate some of the evaluation items [1] to [10] as evaluation value elements and combine them to calculate one evaluation value. In the latter case, the evaluation value calculating function 743 may calculate a single evaluation value by simple averaging or simple addition of evaluation value elements, or may calculate one evaluation value by weighted average or weighted addition of evaluation value elements. For example, the weighting is to make the weight of the evaluation value element, which is estimated to be more important to the operator among evaluation value elements, heavier than the other evaluation value elements.

The parameter calculating function 744 includes a function equivalent to the parameter calculating function 444 shown in FIG. 2. The parameter calculating function 744 is an example of a parameter calculating unit.

The display-used image acquiring function 745 includes a function equivalent to the display-used image acquiring function 445 shown in FIG. 2. The display-used image acquiring function 745 is an example of a display-used image acquiring unit.

The parameter acquiring function 746 includes a function equivalent to the parameter acquiring function 446 shown in FIG. 2. The parameter acquiring function 746 is an example of a parameter acquiring unit.

The display control function 747 includes a function equivalent to the display control function 447 shown in FIG. 2. The display control function 747 is an example of a display control unit.

The memory control function 748 includes a function equivalent to the memory control function 448 shown in FIG. 2. The memory control function 748 is an example of a memory control unit.

It should be noted that the operation of the medical image processing apparatus 70 is the same as the operation of the console 40 shown in FIGS. 9 and 10.

As described above, according to the medical image processing apparatus 70, it is easy for the operator to observe an image in the vicinity of the z-position including the attention region in daily image-confirmation operations such as an image inspection and a screening examination, while reducing the load on the operator in fine adjustment operation of the displayed image during image observation. The image inspection means an image check or editing operation for facilitating diagnosis. Further, according to the medical image processing apparatus 70, the displayed image near the z-position including the attention region is slowly forwarded/reversed by one operation. Thereby, even when the specific displayed image is not observed attentively after the operator has operated from the beginning to the end of multiple images and stopped forwarding/reversing, the displayed image near the z-position including the attention region is likely to remain in the operator's consciousness. As described above, according to the medical image processing apparatus 70, it is possible to efficiently present desired displayed image data to the operator from among the multiple displayed image data, so that diagnostic efficiency is improved.

3. First Modification

The display control function 747 (or the display control function 447) may adjust the calculated sensitivity parameter according to a difference between a slice interval in the z-axis direction in first multiple display-used image data and a slice interval in the z-axis direction in second multiple display-used image data.

FIG. 12 is a diagram for explaining adjustment of the sensitivity parameter.

For example, when the display control function 747 displays the second multiple display-used image data in parallel with the first multiple display-used image data and operates both, the operator should want to have both displayed them so that the z-position of the displayed image of the first multiple display-used image data is the same as the z-position of the displayed image of the second multiple display-used image data. Therefore, the display control function 747 adjusts both or one of the sensitivity parameters according to the difference in slice interval so that displayed images display the same z-position.

Thus, according to the first modification, the diagnostic efficiency is further improved by adjusting the sensitivity parameter.

4. Second Modification

Although the slice image data of the axial cross section is described as an example of each medical image data, the present invention is not limited to this case. For example, the X-ray CT apparatus can generate multiple slice image data having a certain angle from the axial cross section in a tilted state. In that case, the evaluation value calculating function 443 calculates an evaluation value in accordance with a distance in the z-axis direction from the above-described attention. In addition to the axial cross section, the MRI apparatus can generate multiple slice image data of a sagittal cross section or a coronal cross section. In this case, the evaluation value calculating function 443 calculates an evaluation value according to a distance in the x-axis direction (direction perpendicular to the sagittal cross section) or the y-axis direction (direction perpendicular to the coronal cross section) from the above-described attention region. The MRI apparatus can also generate multiple slice image data of oblique cross sections. In this case, the evaluation value calculating function 443 calculates an evaluation value according to a distance from the region of interest in a direction orthogonal to the slice.

Furthermore, volume data may be generated based on multiple slice image data generated in the medical image diagnostic apparatus. In this case, the evaluation value calculating function 443 may calculate an evaluation value according to a distance from the attention region in a direction orthogonal to a multi-planar reconstruction (MPR) cross section. For example, when the medical image diagnostic apparatus is an X-ray CT apparatus, the volume data may be CT volume data based on a CT scan, or be scano data based on "three-dimensional scano imaging", which is a pre-scan performed prior to the execution of CT scan.

The "three-dimensional scano imaging" means a scan performed by rotating the X-ray tube and the X-ray detector around the patient, while moving the table on which the patient is placed with respect to the gantry (or moving the gantry with respect to the table). The "three-dimensional scano imaging" is also called "helical scano". For example, the "three-dimensional scano imaging" is performed in order to determine the X-ray modulation conditions at the later CT scan.

Thus, according to the second modification, it is possible to calculate the evaluation value according to not only the distance in the z-axis direction from the attention region but also the distance in the other directions.

5. Third Modification

The cross-sectional direction of each calculation-used image data acquired by the calculation-used image acquiring function 442 and the cross-sectional direction of each display-used image data acquired by the display-used image acquiring function 445 may be different. For example, each calculation-used image data may be image data of an axial cross section, while each display-used image data may be image data of a sagittal cross section or an MPR cross section.

In this case, the evaluation value calculating function 443 can calculate an evaluation value when generating calculation-used axial cross-sectional image data according to a distance from the attention region in the direction perpendicular to the display-used sagittal cross section or MPR cross section. For example, as described above, when the volume data is generated based on the display-used axial cross-sectional image data, the evaluation value calculating function 443 calculates the evaluation value based on the volume data according to a distance from the attention region in the direction perpendicular to the display-used sagittal cross section or MPR cross section.

6. Fourth Modification

An example has been described in which multiple calculation-used image data are acquired by the calculation-used image acquiring function 442 and each acquired calculation-used image data is slice image data of an arbitrary cross section including an axial cross section. However, it is not limited to this case. For example, one calculation-used image data may be acquired by the calculation-used image acquiring function 442, and one calculation-used image data may be scano image data (two-dimensional or three-dimensional scano image data). The X-ray CT apparatus can generate two-dimensional scano image data by performing two-dimensional scano imaging projected onto the y-z plane or the z-x plane, or perform three-dimensional scan imaging as described above. The scano image data is also called "positioning image data" or "scout image data". Next, a method for calculating an evaluation value when the calculation-used image data is scano image data will be described.

First, the X-ray CT apparatus sets a scan range on the scano image and sets a helical pitch for each corresponding scan range. Therefore, the evaluation value calculating function 443 is possible to acquire each evaluation value in the z-axis direction when calculating the evaluation value using the helical pitch of the above [1], by using the helical pitch (evaluation value) assigned to the z-axis direction of the scano image data.

Secondly, the X-ray CT apparatus calculates a tube current that seems to be necessary for obtaining a certain image quality based on a pixel value on a cross section or a line orthogonal to the z-axis of the scano image, thereby adjusts the tube current when actually imaging. The X-ray CT apparatus sets the adjusted tube current value at each position in the z-axis direction. That is, since the tube current (evaluation value) is assigned to the z-axis of the scano image data, the evaluation value calculating function 443 is possible to calculate each evaluation value in the z-axis direction, using the tube current of the above [1].

Thirdly, the X-ray CT apparatus can automatically detect the attention region from the scano image data, or can manually set the attention region according to an operator's designation, thereby recognize the position of the attention region in the z-axis direction. Therefore, the evaluation value calculating function 443 is able to acquire each evaluation value in the z-axis direction when calculating the evaluation value using the ROI of the above [2] on the basis of the z-axis distance from the ROI on the scano image.

7. Fifth Modification

Although the case where multiple slice image data with different positions served as the multiple medical image data is described, the present invention is not limited to this case. For example, the multiple medical image data may be multiple slice image data having different imaging times, multiple slice image data having different positions and imaging times, or multiple three-dimensional image data having different positions and imaging times. The three-dimensional image data includes MPR image data, projection image data obtained by projecting volume data according to the viewpoint and the projection direction, and the like.

Each of FIGS. 13A and 13B is a diagram for explaining sensitivity parameters for multiple three-dimensional image data having different positions and imaging times. Each of FIGS. 13A and 13B shows a case where virtual endoscopy (VE) image data capable of observing inside a lumen is used as medical image data.

The display method of the VE image refer to be a flythrough-display that displays a moving image of the VE image by moving the viewpoint along the core line of the lumen body. For example, when performing the fly-through display of a mammary gland using an ultrasonic diagnostic apparatus, the operator applies an ultrasonic probe (mechanical scan probe, etc.) capable of three-dimensional scanning to the breast of the patient and "volume data including the mammary gland" is acquired. By extracting a pixel (voxel) having a luminance value corresponding to the luminance value of the lumen body, a region B of lumen body is extracted from the volume data. Next, the extracted region B of lumen body is thinned to extract a core line C of lumen body. Next, VE image data from the viewpoint V on the core line C is generated by a perspective projection method. Multiple VE image data for fly-through display is generated by moving the viewpoint along the core line C of lumen body (shown in FIG. 13A).

The calculation-used image acquiring function 742 acquires the multiple VE image data (shown in FIG. 13B). Then, the evaluation value calculating function 743 calculates evaluation values of the multiple VE image data acquired by the calculation-used image acquiring function 742. Further, the parameter calculating function 744 calculates a sensitivity parameter indicating the forwarding/reversing number of displayed images for the operation amount of the multiple VE image data to be displayed on the basis of the evaluation value calculated by the evaluation value calculating function 743.

As described above, according to the fifth modification, it is possible to efficiently acquire not only the multiple slice image data having different positions but also multiple three-dimensional image data having different positions and imaging times, and represent it to the operator, so that diagnostic efficiency is improved.

8. Other Modifications

Whether or not to apply the sensitivity parameter to the multiple display-used image data may be configured to be switched by the input interface 73 (or input interface 43) such as a switch operated by an operator.

Further, there is a case where the operator performs observation again after observing the multiple medical image data without applying the sensitivity parameter to the multiple display-used image data. In this case, the display control function 747 (or the display control function 447) may apply the sensitivity parameter only around the z-position where the first observation time is short among the z-positions having high evaluation values. Alternatively, in order to prevent oversight, the display control function 747 (or the display control function 447) may separately display the z-position where the first observation time is short as the "missed area" on the screen.

The display control function 747 (or the display control function 447) may apply the sensitivity parameter only to the z-position corresponding to the evaluation value within a specific threshold range as one of the sensitivity parameter adjustment methods.

The display control function 747 (or the display control function 447) may display the medical image data corresponding to the evaluation value within a specific threshold range on the screen as an Insert image. The Insert image is an image obtained by changing elements other than the sensitivity parameter, such as zoom ratio, resolution, ratio "WW (Window Level)/WL (Window Width)", and thickness. It goes without saying that the display on the original image side may be changed instead of the Insert image.

The display control function 747 (or the display control function 447) may display character information indicating the reason why the sensitivity parameter is applied on the display screen. An example of the character information is "during highlighting of the attention region".

There can be cooperation between CT image data and image data acquired by another medical image diagnostic apparatus such as an MRI apparatus or a PET apparatus. For example, ROI is set for calculation-used CT image data corresponding to a region where bleeding has occurred among the calculation-used CT image data. In this case, the medical image processing apparatus 70 sets a high evaluation value for an MR image data corresponding to the z-position of the calculation-used CT image data in which the ROI is set, the MR image data being among the multiple MRI image data.

According to at least one embodiment described above, it is possible to improve diagnosis efficiency by efficiently acquiring a desired medical image from the medical images and presenting it to the operator.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
acquire medical images,
calculate sensitivity parameters based on an evaluation value corresponding to each of the respective medical images, the sensitivity parameters each indicating forwarding/reversing number or forwarding/reversing speed of displayed images according to a unit amount of operation, and
control, based on the sensitivity parameters and an input operation amount, a forwarding/reversing number or a forwarding/reversing speed of the medical images thereby updating a displayed image of the medical images based on the controlled forwarding/reversing number or forwarding/reversing speed.

2. The medical image processing apparatus according to claim 1, wherein the processing circuitry is configured to calculate the sensitivity parameters of the medical images according to distances from an attention region.

3. The medical image processing apparatus according to claim 2, wherein the processing circuitry is configured to estimate the attention region based on at least one of: a helical pitch related to a helical scan: a tube current of an X-ray tube; an amount of X-ray exposure; a difference value from a past image; an observation time on a past image observation time; and a pixel value of a medical image.

4. The medical image processing apparatus according to claim 2, wherein the processing circuitry is configured to estimate the attention region based on a region of interest (ROI) set in at least one of medical images.

5. The medical image processing apparatus according to claim 2, wherein the processing circuitry is configured to estimate the attention region based on a result value from an analysis algorithm.

6. The medical image processing apparatus according to claim 1, wherein the processing circuitry is configured to calculate the sensitivity parameters of the medical images according to reconstruction conditions of the medical images.

7. The medical image processing apparatus according to claim 1, wherein the processing circuitry is configured to estimate a state that requires partial re-imaging, and calculate the sensitivity parameters of the medical images according to the state.

8. The medical image processing apparatus according to claim 7, wherein the processing circuitry is configured to calculate the sensitivity parameters of the medical images according to the state of a subject in a scanning when the medical images have been acquired.

9. The medical image processing apparatus according to claim 1, wherein the processing circuitry is configured to calculate the sensitivity parameter for each of the medical images based on plural sensitivity parameter elements.

10. The medical image processing apparatus according to claim 9, wherein the processing circuitry is configured to calculate the sensitivity parameters by performing simple average, simple addition, weighted average, and weighted addition of at least two of the plural sensitivity parameter elements.

11. The medical image processing apparatus according to claim 1, wherein the processing circuitry is configured to select any one of plural sensitivity parameter elements as the sensitivity parameter.

12. The medical image processing apparatus according to claim 1, wherein
the processing circuitry is configured to
acquire calculation-used medical images for acquiring the sensitivity parameters, and
acquire display-used medical images for display,
the display-used medical images are same as the calculation-used medical images, or are extracted from the calculation-used medical images.

13. The medical image processing apparatus according to claim 1, wherein
the processing circuitry is configured to
acquire calculation-used medical images for acquiring the sensitivity parameters, and
acquire display-used medical images for display,
the display-used medical images are different in type from the calculation-used medical images.

14. The medical image processing apparatus according to claim 1, wherein
the processing circuitry is configured to
acquire calculation-used medical images for acquiring the sensitivity parameters, and
acquire display-used medical images for display,
the display-used medical images have different cross-sectional directions from the calculation-used medical images.

15. The medical image processing apparatus according to claim 1, wherein
the processing circuitry is configured to
acquire calculation-used medical images for acquiring the sensitivity parameters, and
acquire display-used medical images for display,
the calculation-used medical images is scan image data.

16. The medical image processing apparatus according to claim 1, wherein the medical images are images having different positions or having at least different imaging times.

17. The medical image processing apparatus according to claim 1, wherein the processing circuitry is configured to further display character information indicating a reason why the sensitivity parameters are applied.

18. The medical image processing apparatus according to claim 1, wherein
the processing circuitry is configured to
calculate an interval to be stored of the medical images based on the sensitivity parameters, and
store the medical images in a memory according to the interval.

19. A method for processing a medical image comprising steps of:
acquiring medical images;
calculating sensitivity parameters based on an evaluation value corresponding to each of the respective medical images, the sensitivity parameters each indicating forwarding/reversing number or forwarding/reversing speed of displayed images according to a unit amount of operation; and
controlling, based on the sensitivity parameters and an input operation amount, a forwarding/reversing number or a forwarding/reversing speed of the medical images, thereby updating a displayed image of the medical images based on the controlled forwarding/reversing number or forwarding/reversing speed.

20. A non-transitory computer readable medium storing a computer program realizing functions of:
acquiring medical images;
calculating sensitivity parameters based on an evaluation value corresponding to each of the respective medical images, the sensitivity parameters each indicating forwarding/reversing number or forwarding/reversing speed of displayed images according to a unit amount of operation; and
controlling, based on the sensitivity parameters and an input operation amount, a forwarding/reversing number or a forwarding/reversing speed of the medical images, thereby updating a displayed image of the medical images based on the controlled forwarding/reversing number or forwarding/reversing speed.

* * * * *